United States Patent [19]
Maekawa et al.

[11] Patent Number: 5,919,448
[45] Date of Patent: Jul. 6, 1999

[54] PLANT GROWTH REGULATOR

[75] Inventors: Yoshio Maekawa, Miki; Yukihiko Yoshimi, Kakogawa; Taizoh Akiyama, Takasago, all of Japan

[73] Assignee: Taki Chemical Co., Ltd., Hyogo-ken, Japan

[21] Appl. No.: 09/027,627

[22] Filed: Feb. 23, 1998

[30]     Foreign Application Priority Data

Apr. 15, 1997  [JP]  Japan .................................... 9-114277

[51] Int. Cl.⁶ ............................ A01N 1/20; A01N 63/00; C12N 11/00; C12N 11/14
[52] U.S. Cl. ...................... 424/93.47; 435/174; 435/176; 435/252.1; 435/252.34; 435/876
[58] Field of Search ........................... 435/252.1, 252.34, 435/174, 176, 876; 434/93.47

[56]                References Cited

PUBLICATIONS

Derwent Abstract of WPI Acc No. 98–010805/199802—Abstract (Basic) EP 808571 A Corresponding to JP 96149988 A.

*Primary Examiner*—Herbert J. Lilling
*Attorney, Agent, or Firm*—Wenderoth, Lind & Ponack L.L.P.

[57]                 ABSTRACT

Disclosed herein is plant growth regulator comprising an isolated Pseudomonas fluorescens FPT-9601 strain or an isolated Pseudomonas sp. FPH-9601 strain which are endosymbiotic pseudomonads.

7 Claims, No Drawings

PLANT GROWTH REGULATOR

BACKGROUND OF THE INVENTION

1. Field of the Invention

The present invention relates to a plant growth regulator and an object of the present invention is that said regulator is (1) able to suppress a spindly growth especially at the stage of raising the crop plants, (2) able to improve the long-term storage of seedling and (3) able to conduct an efficient regulation of raising of seedling whereby improvement in productivity of agricultural products is aimed.

2. Description of the Related Art

In recent years, agricultural techniques have been directed, both domestic and abroad, to the agriculture of an environment-protecting type and there has been a demand for agricultural technique which is friendly to ecology. Under such circumstances however, it is still the present status that agricultural chemicals are used for prevention of plant diseases and that they are used for regulation of growth of plants as well. Accordingly, when the problem on the safety of agricultural chemicals is further taken into consideration, the present situation is far from the aim of the agriculture of an environment-protecting type.

The agents which are used for the regulation of growth of plants at present are plant growth regulators and their efficacies in promotion of rooting, making the seedlings healthy, prevention of injury at planting, promotion of generation of lateral buds, suppression of axillary buds, promotion of flowering, bearing, thickening, coloration and ripening time, retardation of growth (dwarfing), prevention of fruit drop, prevention of fruit thinning and russet fruit, prevention of phytotoxicity, promotion of adhesion, etc. However, most of the agents are agricultural chemicals mainly comprising synthetic compounds.

Among them, the plant growth regulators used for the retardation of growth (dwarfing) are ancymidol preparations, dikegulac preparations, daminozide preparations, mefluidide preparations, chlormequat liquid preparations, paclobutrazol granules, inabenfide granules, etc. However, all of them contain synthetic compounds as the main ingredients and their use is limited to flowers and ornamental plants, garden plants, fruits and nuts, turf, wheat and rice plant only. Since efficacy of many of the components are dependent upon the concentration upon use, knowledge and experience are required for avoiding the phytotoxicity and choosing the stage of use.

On the other hand, due to a decrease or advancing ages in people for agricultural works or due to a governmental policy of reduction of cultivating field for rice plant in recent years, plan of making the agricultural works efficient and conversion to cultivation of highly value-added field farm products are now being forwarded and, with respect to the object of use of plant growth regulators, utilization meeting with such a change in circumstance is now going on. Thus, in cultivation of leaf and stem vegetables and fruit vegetables which are in an increasing demand, division of labor and utilization of machines in agricultural works are now in progress using cell raised seedling whereby farmers do not prepare seedlings by themselves but purchase the seedlings from other manufacturers who are specialized in raising the seedlings and then said seedlings are cultivated by the farmers for harvest. Under such a system, farmers have no burden for raising the seedling but can devote themselves to just cultivation. Moreover, in leaf and stem vegetables, mechanical planting technique has been developed already for cell raised seedling and, therefore, plan of making the agricultural work efficient and conversion to highly value-added cultivation have been smoothly going on.

However, the biggest disadvantage of this cell raised seedling is that raised seedling grows spindlingly. Especially in a high temperature period such as in summer, spindly growth is significantly accelerated and, when preparation of the field for cultivation is delayed even for a short while, the resulting seedlings are sometimes unable to be used. In addition, plantation by machines is difficult for spindlingly grown seedlings and there is a problem in rooting of the seedling upon transplantation to the final field. Accordingly, there has been a brisk demand for development of dwarfing agents during the seedling stage which are effective for such plants.

As such, there has been a demand for developing an effective dwarfing agent which is a plant growth regulator avoiding the problem of safety in agricultural chemicals and the like, meeting with the trend of agriculture to an environment-protecting type and suppressing the spindly growth of raised seedling in cell raised seedling effective in making the agricultural works efficient and in conversion to highly value-added cultivation. However, at present, such a technique has not been developed yet.

In the meanwhile, the present inventors established a growing technique of disease tolerance seedling by the utilization of two specific strains mutualistically colonizing in the roots of crop plants and already filed a patent application entitled "Plug Mixture for Raising Seedlings and Method for Producing It, and Method for Raising Disease Tolerance Seedlings" (Japanese Patent Application Number Hei-08/149,988). During the course of investigations of a growing technique of such disease tolerance seedlings, the present inventors have found that both of those two specific strains exhibit an excellent dwarfing effect during the growing stage of the seedling of plants and achieved the present invention based upon such a finding.

SUMMARY OF THE INVENTION

Thus, the present invention relates to a plant growth regulator consisting of *Pseudomonas fluorescens* FPT-9601 strain or Pseudomonas sp. FPH-9601 strain belonging to endosymbiotic pseudomonads. In accordance with the present invention, spindly growth of seedlings of raising stage can be suppressed by a dwarfing technique using those strains whereby an efficient control of seedling raising can be achieved. In addition, productivity of agricultural products is aimed by the effective control of raising of seedling as such. Further, because of the use of microbes, the problem of safety to human being, animals and environmental animals and plants by the use of agricultural chemicals and the like can be solved. Thus, the present invention relates to a plant growth regulator of great use.

DESCRIPTION OF THE PREFERRED EMBODIMENT

As hereinafter, the plant growth regulator of the present invention will be mentioned in detail. The plant growth regulator of the present invention is characterized in the use of a microorganism consisting of *Pseudomonas fluorescens* FPT-9601 strain or Pseudomonas sp. FPH-9601 strain belonging to endosymbiotic pseudomonads.

Hereunder, the individual activities of these endosymbiotic pseudomonads, i.e. *Pseudomonas fluorescens* FPT-9601 strain (hereinafter, just referred to as Ps. FPT) and Pseudomonas sp. FPH-9601 strain (hereinafter, just referred to as Ps. FPH) will be described in detail.

According to Bergey's Manual of Systematic Bacteriology, Volume 2, 1986, Ps. FPT is classified under a group of *Pseudomonas fluorescens* biotype IV in view of its taxonomical characteristics which will be mentioned later and is characterized in producing crystalline 2,4-diacetylphloroglucinol which is an antibiotic substance. This microbe Ps. FPT is of a type of psychrotrophic and oligotrophic bacteria having especially high rate of inocula colonization in the endorhizosphere of crop plants of Solanaceae and Cruciferae.

On the other hand, another microbe Ps. FPH is a strain similar to both *Pseudomonas chlororaphis* and *Pseudomonas fluorescens* in view of its taxonomical characteristics which will be mentioned later and is a type of psychrotrophic bacteria having specially high rate of inocula colonization in the endorhizosphere of crop plants of Solanaceae. In addition, Ps. FPH is characterized in producing fluorescent slime.

These endosymbiotic pseudomonads, i.e. Ps. FPT and Ps. FPH, were isolated from the endorhizosphere of tomato (of a variety of Kantaro Jr.) in a crop field having a soil-borne disease of tomato bacterial wilt in Aboshi-ku, Himeji-shi, Hyogo-ken, Japan. Both of those two strains have been deposited in the National Institute of Bioscience and Human-Technology, Agency of Industrial Science and Technology (1–3, Higashi 1 chome, Tsukuba-shi, Ibaraki-ken, 305 Japan) under a microbe deposition code number FERM BP-5478 for Ps. FPT and a microbe deposition code number FERM BP-5479 for Ps. FPH on Mar. 21, 1996.

Now, the taxonomical characteristics of the strain Ps. FPT will be mentioned in detail as hereunder.
a) Morphological Characteristics:
Gram-negative rod of 0.5–1.0 $\mu$m×1.5–2.0 $\mu$m
Motility: +
motile by polar fragella
Endospore formation: –.
b) Growing Condition:
This microbe forms circular, flat and cream-colored colonies in a PDA medium within 3 to 4 days.
(PDA medium: a medium prepared by diluting potato dextrose 3- to 5-fold and adding 1.5% of agar thereto)
c) Physiological Characteristics:
Production of 2,4-diacetylphloroglucinol: produced in crystals
Viability temperature: 15 to 35° C. (cells of this strain are aggregated at 37° C.)
OF test (glucose oxidation/glucose fermentation test): oxidative
Cytochrome oxidase reaction: –/±[within a period of ordinary detection, the reaction is minus (–)]
Nitrate reduction: denitrification
Indole production: –
Hydrogen sulfide production: –
Acetoin production: +
Levan formation from sucrose: +
L-Arginine dihydrase: +
Urease: –
Gelatin liquefaction: +
α-Glucosidase: –/±
β-Glucosidase: ±/–
β-Galactosidase: –
Acid production: from citric acid, glucose, sucrose, D-melibiose, L-arabinose
Carbon sources for growth: Glucose, L-arabinose, D-mannose, D-mannitol, N-acetyl-D-glucosamine, potassium gluconate, n-capric acid, dl-malic acid, sodium citrate.

Next, the taxonomical characteristics of another strain Ps. FPH will be mentioned in detail as hereunder.
a) Morphological Characteristics:
Gram-negative rod of 0.2–0.5 $\mu$m×1.0–1.5 $\mu$m
Motility: +
motile by polar fragella
Endospore formation: –.
b) Growing Condition:
This microbe forms circular, flat and cream-colored colonies in a PDA medium within 2 to 3 days.
c) Physiological Characteristics:
Production of fluorescent slime: +
Viability temperature: 15 to 37° C.
OF test (glucose oxidation/glucose fermentation test): –
Cytochrome oxidase: +
Nitrate reduction (for producing nitrites from nitrates): +
Indole production: –
Hydrogen sulfide production: –
Acetoin production: –
Levan formation from sucrose: –
L-Arginine dihydrase: –
Urease: –
Gelatin liquefaction: –
α-Glucosidase: –
β-Glucosidase: +
β-Galactosidase: –
Acylamidase: +
Acid production: from citric acid
Carbon sources for growth: Glucose, D-mannose, D-mannitol, N-acetyl-D-glucosamine, potassium gluconate; dl-malic acid, sodium citrate, phenyl acetate, ethanol.

Next referred to is a method for incubating Ps. FPT and Ps. FPH. Both Ps. FPT and Ps. FPH can be incubated in the same manner. For example, cells of the two strains are statically incubated in a liquid medium containing 0.8 g/liter of potato extract and 4 g/liter of glucose at 25° C. for two weeks to obtain propagated cells of said two strains, i.e. Ps. FPT and Ps. FPH.

Those microbial cells may be practically used in a state of an incubated liquid after the incubation or of dried cell prepared by drying the liquid but, in order to maintain a stable effect and durability, it is recommended to use the incubated cell after imobilizing with a carrier such as vermiculite, zeolite, silica and diatomaceous earth. Alternatively, they may be immobilized with agricultural materials such as plug mixture for raising seedling which is prepared by mixing loam or humic soil with vermiculite or peat moss.

With regard to the cell concentration upon actual use, the concentration is preferably not less than $10^4$ cfu/g or, more preferably, not less than $10^5$ cfu/g when the incubated liquid per se or dried cell is used. When a carrier or a plug mixture for raising seedling is applied, the preferred cell concentration in the carrier or the plug mixture is similar to the above, i.e. preferably not less than $10^4$ cfu/g or, more preferably, not less than $10^5$ cfu/g.

With regard to the upper limit of the cell concentration, it is usually up to $10^{10}$ cfu/g and, even if the concentration is made higher than that, there is no longer additional good effect and, in addition, it is rather uneconomical.

In the case of a method where both microbial cells are immobilized in a carrier or in a plug mixture followed by incubating, the cell concentration usually becomes not less than $10^5$ cfu/g when the strain is inoculated in the carrier or the plug mixture and incubated in a sterile room at 15–30° C. for around three weeks.

The main object of the plant growth regulator of the present invention is to afford an effect of dwarfing the plants. The method of using the regulator of the present invention as such is that the carrier or the plug mixture wherein the incubated liquid or the cell which is immobilized as mentioned above is directly mixed with the seeds of the plant to be dwarfed, then a field or a plug mixture is sowed with the above-mixed seeds and a cultivation is conducted. Depending upon the type of the farm products to be cultivated, it is also possible to directly sprinkle the suspension of the cell on leaves of the young plant.

The farm products for which the present invention is especially effective are those of Solanaceae, Cruciferae and Cucurbitaceae or, to be more specific, tomato, green pepper, eggplant, celery cabbage, cabbage, chingensai (a kind of Chinese cabbage), cucumber, wheat, rice plant, corn, etc. although the present invention is not limited thereto.

EXAMPLES

The present invention will now be further illustrated by way of the following examples in which the term "%" is that by weight throughout the specification unless otherwise specifically mentioned. Incidentally, in the present invention, both Ps. FPT and Ps. FPH are bacteria and, in the Examples, microbial cell concentration is given in terms of the numbers of mobile cells directly counted under a microscope. Thus, the unit of the cell concentrations expressed in terms of cfu/g and cells/ml are substantially same and, accordingly, it will be hereinafter expressed in terms of cell/ml in the case of a suspended liquid containing the cell.

Example 1.

Dwarfing test of tomato seedlings was conducted under the following condition using the plant growth regulator of the present invention. An agar medium of White (no sucrose being added) (15 ml), 3 ml of sea sand and 5 ml of 0.8% agar were formed in lower, medium and upper layers, respectively, of an incubating bottle with an outer diameter of 2.5 cm and a height of 15 cm having a cover. Various kinds of tomato seeds were dipped in a 80% aqueous solution of ethanol for one minute and then dipped in a 1% aqueous solution of sodium hypochlorite for ten minutes to sterilize the seed. Each of the above-mentioned bottles was sowed with each of the resulting sterile seeds. The varieties of the tomato used were Momotaro, Ogata Fukuju, Koko, Zuiken, Helper M, LS-89 and PFN No.2. The bottles sowed with each kind of the seeds were incubated in a dark place at 28° C. for four days to conduct a forced sprouting and then transferred into a phytotoron to continue the cultivation at 30° C. for three days.

Each of the strains of Ps. FPT and Ps. FPH which are the plant growth regulators of the present invention was made into a suspension preparation containing $10^8$ cells/ml and was inoculated on the surface of the medium of the incubating bottle to make it 5 v/v% to the volume of the medium. After the inoculation, cultivation was further conducted in the phytotoron for 20 days. Incidentally, tomato seeds to which cell-free suspension was inoculated were also cultivated by the same manner. Plant height of each of the tomato seedlings was measured after cultivating for 20 days and the dwarfing rate of the tomato seedling was calculated by the following formula from the plant height of the control seedlings which were cultivated without inoculation of the cell. Twenty tomato seedlings were cultivated for one test group and the calculation of dwarfing rate was conducted from the averages plant heights of each 20 seedlings of test group and control group.

Dwarfing Rate (%)=[(1—Average Plant Height (cm) of the Test Group of this Invention)/(Average Plant Height (cm) of the Control Group)]×100.

The result is shown in Table 1.

TABLE 1

| Variety of Tomato | Inoculated Strain | Average Plant Height (cm) Test Group | Average Plant Height (cm) Control Group | Dwarfing Rate (%) |
|---|---|---|---|---|
| Momotaro | Ps. FPT | 5.6 | 8.9 | 37.0 |
| Ohgata Fukuju | Ps. FPT | 5.9 | 9.3 | 36.6 |
| Koko | Ps. FPT | 6.1 | 9.1 | 33.0 |
| Zuiken | Ps. FPH | 5.8 | 8.7 | 33.3 |
| Helper-M | Ps. FPH | 5.7 | 9.6 | 40.6 |
| LS-89 | Ps. FPH | 4.6 | 10.5 | 56.2 |
| PFN No.2 | Ps. FPH | 5.4 | 9.0 | 40.0 |

Example 2.

Vermiculite, Akadama soil and commercially available plug mixture for raising seedling (manufactured by Taki Chemical Co.; trade name: Taki Plug Mixture for Horticulture) were mixed in a ratio of 18:8:1 by volume and heated at 180° C. for one hour to give a plug mixture for raising seedling. A suspension of $10^6$ cells/ml of Ps. FPT was added to the above plug mixture at the rate of 20 v/v% and allowed to stand at 25° C. for two weeks to prepare a Ps. FPT-immobilized plug mixture. On the other hand, sterile water was added at the rate of 20 v/v% to the above heat-treated plug mixture followed by allowing to stand at 25° C. for two weeks to give a control plug mixture. Each of the Ps. FPT-immobilized plug mixture and the control plug mixture were filled in a tray for cell raised seedling (with 200 holes; manufacture by TLC of U.S.A.), well irrigated and sowed with seeds of each of the varieties of tomato, green pepper, eggplant, celery cabbage, cabbage, chingensai and cucumber.

After sowing, the surface of tray was covered with vermiculite, irrigated, incubated at 28° C. under a dark condition to hasten the germination and cultivated in a greenhouse for the period as shown in Table 2. For comparison, the same cultivation test was conducted using the above control plug mixture (control group). Incidentally, the test was conducted by cultivating each 20 seedlings of the plants for one test group and, in both test group and control group, dwarfing rate was calculated from the average height of the 20 plants by the same manner as in Example 1. The result is shown in Table 3.

TABLE 2

| Kind of Cultivated Plants | Cultivated Days |
|---|---|
| Tomato | 28 |
| Green Pepper | 40 |
| Eggplant | 40 |
| Celery cabbage | 30 |
| Cabbage | 30 |
| Chingensai | 30 |
| Cucumber | 20 |

TABLE 3

| Name of Plant | Name of Variety | Average Height of Plant (cm) | | Dwarfing Rate (%) |
|---|---|---|---|---|
| | | Test Group | Control Group | |
| Tomato | Momotaro | 4.7 | 18.0 | 73.9 |
| | House Momotaro | 7.8 | 17.5 | 55.4 |
| | Momotaro T-93 | 7.0 | 17.2 | 59.3 |
| | Kanpuku | 5.4 | 15.9 | 66.0 |
| | Kantaro Jr. | 6.8 | 15.7 | 56.7 |
| | Koko | 6.8 | 15.0 | 54.7 |
| | Ogata Fukuju | 7.9 | 10.0 | 21.0 |
| | Merry Road | 7.5 | 17.3 | 56.6 |
| | Anchor T | 5.4 | 8.6 | 37.2 |
| | Kage Musha | 6.8 | 10.7 | 36.4 |
| | BE Okitsu #101 | 4.4 | 7.6 | 42.1 |
| | PFN No.1 | 3.7 | 7.2 | 48.6 |
| | Joint | 5.3 | 7.6 | 30.3 |
| | Balcan | 4.3 | 8.1 | 46.9 |
| Green Pepper | Kyonami | 4.3 | 7.5 | 42.7 |
| Eggplant | Senryo #2 | 5.1 | 7.1 | 28.2 |
| Celery cabbage | Musoh | 4.0 | 5.8 | 31.0 |
| Cabbage | Matsunami | 4.2 | 5.5 | 23.6 |
| Chingensai | Seitei | 4.1 | 5.3 | 23.0 |
| Cucumber | Hayamidori | 10.2 | 15.2 | 32.9 |

Example 3.

Ps. FPT which is a plant growth regulator of the present invention was suspended to prepare suspensions of $10^4$ cells/ml, $10^5$ cells/ml, $10^6$ cells/ml, $10^7$ cells/ml and $10^8$ cells/ml and each of them was added to and mixed with vermiculite (manufactured by Hiruishi Kagaku Kogyo K. K.; trade name: Hirukon S-1) which was subjected to a dry heat sterilization to give a mixture containing 20 v/v% of the suspension. This was allowed to stand at 25° C. for two weeks to prepare Ps. FPT-immobilized vermiculite having various concentrations of Ps. FPT. Cell suspensions of Ps. FPH were subjected to the same operation to prepare Ps. FPH-immobilized vermiculite having various cell concentration of Ps. FPH.

Alluvial soil (4 parts) and 1 part of peat moss were mixed to prepare a plug mixture for raising seedlings and the resulting plug mixture was filled in a tray of the cell raised seedling which was the same as that of Example 2. After filling, watering was fully conducted and the upper part of the filled plug mixture was tramped with the bottom of the tray of the same type. Then, the tramped surface of the plug mixture was sowed with seeds of tomato (House Momotaro) and celery cabbage (Muso). After sowing, the surface was covered with the above-mentioned vermiculite in which Ps. FPT or Ps. FPH was immobilized.

In the meanwhile, vermiculite which was subjected to a dry heat sterilization and on which the cell was not immobilized was used as a control plug. After covering with soil, watering was fully conducted and the tray after sowing was placed in a dark and aerobic condition at 28° C. to conduct hastening of germination. Incidentally, those tests were conducted by sowing 100 seeds per test group.

The tray after germination was transferred to a greenhouse and subjected to a cell seedling for four weeks. After two weeks from the initiation of the seedling raising, liquid fertilizer (containing 220 mg/liter of nitrogen, 120 mg/liter of phosphorus pentaoxide and 400 mg/liter of potassium oxide) was irrigated at the rate of 500 ml per tray. After four weeks, heights of the grown 80 seedlings per group were measured and average plant height for each plant was calculated. The result is shown in Table 4.

TABLE 4

| | Average Plant Height (cm) of | |
|---|---|---|
| | Tomato | Celery cabbage |
| (Test Group) | | |
| Ps. FPT ($10^4$ group) | 11.2 | 5.6 |
| Ps. FPT ($10^5$ group) | 9.0 | 4.5 |
| Ps. FPT ($10^6$ group) | 8.5 | 4.2 |
| Ps. FPT ($10^7$ group) | 7.9 | 4.0 |
| Ps. FPT ($10^8$ group) | 7.6 | 4.0 |
| Ps. FPH ($10^4$ group) | 10.8 | 5.5 |
| Ps. FPH ($10^5$ group) | 9.8 | 5.1 |
| Ps. FPH ($10^6$ group) | 9.7 | 4.7 |
| Ps. FPH ($10^7$ group) | 8.8 | 4.7 |
| Ps. FPH ($10^8$ group) | 8.5 | 4.6 |
| (Control Group) | 16.5 | 6.3 |

Example 4.

The plant growth regulator of the present invention was used and a dwarfing test was conducted for rice plant (in a seed plot) under the following condition.

Seed rice (name of the variety: Fukuhikari) was selected by means of an ammonium sulfate solution (specific gravity: 1.13 g/ml), wrapped in gauze and dipped for 48 hours in running water to hasten the germination. An appropriate amount of the incubated liquid of a mixture of Ps. FPT and Ps. FPH (containing $10^8$ cells/ml of each of the cells) was taken in a container and the seed rice after germination was dipped therein for one hour. The control group was dipped for one hour in sterile water.

As to a seed-plot, a plastic container in a size of 10 cm×20 cm×10 cm (length×width×height) was used. As to a bed soil, the following three, i.e. loam (trade name: Soil-Up; manufactured by Taki Chemical Co.), pearlite (trade name: Aquasoil; manufactured by Ikegami Shoten K. K.) and rock wool (trade name: Taki Mat; manufactured by Taki Chemical Co.) were used. Each of the above bed soils was filled in the container for seed-plot in the height of 5 cm from bottom and watering was fully conducted.

The seed-plot was sowed with the above-treated seed rice at the rate of 20 seeds/seed-plot and covered with the same bed soil. This was transferred to a phytotoron and the seeds were grown at 25° C. for 30 days. Dwarfing rates were calculated from the average plant height of 20 plant both in test group and control.

TABLE 5

| | Average Height of Plant (cm) | | Dwarfing Rate (%) |
|---|---|---|---|
| | Test Group | Control Group | |
| Loam | 4.2 | 7.1 | 40.8 |
| Pearlite | 5.3 | 10.5 | 49.5 |
| Rock Wool | 5.7 | 9.6 | 40.6 |

Example 5.

Dwarfing test of wheat and corn was conducted under the following condition using the plant growth regulator of the present invention.

Aqueous solution of basic aluminum chloride, finely powdered silicic acid and Ps. FPH were mixed to prepare the cell suspensions of $10^4$, $10^5$, $10^6$, $10^7$ and $10^8$ cells/ml concentrations where all of suspensions contained 0.5% of aluminum oxide and 9.0% of silicon dioxide.

Each 10 ml of this cell suspensions was mixed with 20 ml of wheat seeds (name of the variety: Norin #61) and corn seeds (name of the variety: Honey Bantam Peter 445) and the mixture was dried under vacuum at 30° C. to prepare the seeds coated with Ps. FPH. Incidentally, the seeds to which cell-free suspension was added were used as a control.

Loam was filled in a container of 90 cm×90 cm×50 cm (length×width×height) and a fertilizer was added thereto to make the amounts of nitrogen, phosphorus oxide and potassium oxide 8 g, 17 g and 11 g, respectively, per container. The container was directly sowed with each 20 coated seeds and control seeds, covered with the loam and watering was conducted. Cultivation was conducted outside for 30 days, plant heights of each 20 plant were measured in a test group and in a control group and an average plant height was calculated therefrom. The result is given in Table 6.

TABLE 6

| | Average Plant Height (cm) of | |
|---|---|---|
| | Wheat | Corn |
| (Test Group) | | |
| Ps. FPH ($10^4$ group) | 15.9 | 19.2 |
| Ps. FPH ($10^5$ group) | 14.5 | 17.8 |
| Ps. FPH ($10^6$ group) | 14.3 | 16.4 |
| Ps. FPH ($10^7$ group) | 13.0 | 16.3 |
| Ps. FPH ($10^8$ group) | 12.6 | 16.0 |
| (Control Group) | 24.4 | 22.0 |

Example 6.

Cultivation test of tomato was conducted in a crop field using the plant growth regulator of the present invention and the tomato seedlings which were grown under the following condition.

Thus, seedlings of tomato (name of the variety: Momotaro T-93) were raised in a cell for 28 days as mentioned in Example 2. In the case of a control group, a cell raised seedling system was conducted without adding the cell to the loam. The cell raised seedlings were preliminarily planted to a growing pot and raised for three weeks and the plant height after growth was measured. The resulting seedlings were planted to a farmer's field (Himeji-shi, Hyogo-ken), total harvest of tomato after cultivation of 3–4 months was measured and the harvest per unit area of the field was calculated. The result is shown in Table 7.

TABLE 7

| | Test Group | Control Group |
|---|---|---|
| Plant Height (cm) | | |
| when preliminary planted to pots | 7.6 | 15.8 |
| when planted to the field | 23.9 | 24.3 |
| Harvest (tons/10 ares) | 14.3 | 9.7 |

Example 7.

Cultivating test of wheat was conducted under the following condition using the seeds coated with the plant growth regulator of the present invention.

Coated seeds of wheat (name of the variety: Norin #61) were prepared using a cell suspension containing $10^8$ cells/ml of Ps. FPH in accordance with the manner as mentioned in Example 5. In the meanwhile, the seeds to which cell-free suspension was added were used as a control.

The farmer's crop field (Kasai-shi, Hyogo-ken) was directly sowed with the seeds and the state of growth in initial stage was investigated. Further, total harvest after the harvest was measured and the harvest per unit area of the crop field was calculated. Incidentally, sowing was conducted in this test on the last day of October and harvest was on the last day of May of the next year. The result is shown in Table 8.

TABLE 8

| | Test Group | Control Group |
|---|---|---|
| plant Height (cm) | | |
| on the 15th day from the sowing | 12.2 | 20.5 |
| on the 30th day from the sowing | 25.8 | 24.6 |
| Harvest (tons/10 ares) | 397 | 307 |

Merit of the Invention

The plant growth regulator of the present invention is characterized in using *Pseudomonas fluorescens* FPT-9601 strain or Pseudomonas sp. FPH-9601 strain and, as a result of a dwarfing technique using such strains, spindly growth of seedling in the raising stage can be suppressed whereby an efficient control of raising of seedling can be achieved. In addition, as a result of such an efficient control of raising of seedling, productivity of agricultural products can be improved and, because of the use of microbes, the problem of safety by the use of chemical agents such as agricultural chemicals can be avoided whereby the present invention relates to a plant growth regulator of great use.

What is claimed is:

1. A plant growth regulator comprising an isolated *Pseudomonas fluorescens* FPT-9601 strain or an isolated Pseudomonas sp. FPH-9601 strain.

2. The plant growth regulator according to claim 1, wherein the isolated *Pseudomonas fluorescens* FPT-9601 strain or the isolated Pseudomonas sp. FPH-9601 strain is in a microbial cell concentration of not less than $10^4$ cfu/g.

3. The plant growth regulator according to claim 2, wherein the isolated *Pseudomonas fluorescens* FPT-9601 strain or the isolated *Pseudomonas fluorescens* FPH-9601 strain is in the form of an incubated liquid or dry cells.

4. The plant growth regulator according to claim 2, wherein the isolated *Pseudomonas fluorescens* FPT-9601 strain or the isolated Pseudomonas sp. FPH-9601 strain is immobilized with an immobilizing material.

5. The plant growth regulator according to claim 4, wherein the immobilizing material is selected from the group consisting of vermiculite, zeolite, silica, diatomaceous earth and plug mixture for raising seedling.

6. A method of regulating plant growth comprising mixing the plant growth regulator of claim 1 with seeds of a plant to be regulated.

7. A method of regulating plant growth comprising sprinkling the plant growth regulator of claim 1 on leaves of a plant to be regulated.

* * * * *